United States Patent [19]
Kleese et al.

[11] Patent Number: 5,342,646
[45] Date of Patent: Aug. 30, 1994

[54] METHOD FOR MAKING CARRIER SYSTEMS FOR BIOLOGICALLY ACTIVE MATERIALS

[75] Inventors: Wolfgang Kleese; Dieter Kraemer, both of Mainz; Hans-Ulrich Petereit, Darmstadt; Klaus Lehmann, Rossdorf; Werner Siol, Darmstadt-Eberstadt, all of Fed. Rep. of Germany

[73] Assignee: Röhm GmbH, Darmstadt, Fed. Rep. of Germany

[21] Appl. No.: 979,425

[22] Filed: Nov. 19, 1992

Related U.S. Application Data

[63] Continuation of Ser. No. 745,155, Aug. 15, 1991, abandoned.

[30] Foreign Application Priority Data

Aug. 25, 1990 [DE] Fed. Rep. of Germany ....... 4026992

[51] Int. Cl.$^5$ .................. B05D 7/00; B05D 1/12; A61K 9/16
[52] U.S. Cl. .................. 427/2.1; 427/214; 427/221; 427/421; 427/2.13
[58] Field of Search ................. 427/2, 212, 221, 421, 427/430.1, 220, 214

[56] References Cited

U.S. PATENT DOCUMENTS

| | | | |
|---|---|---|---|
| 4,357,142 | 11/1982 | Schall, Jr. et al. | 427/2 |
| 4,357,363 | 11/1982 | Pierce et al. | 427/2 |
| 4,710,525 | 12/1987 | Kraemer et al. | 525/286 |
| 4,824,640 | 4/1989 | Hildenbrand et al. | 427/2 |
| 4,921,915 | 5/1990 | Dengler et al. | 525/279 |
| 4,945,146 | 7/1990 | Kapmeyer et al. | 526/304 |
| 5,217,492 | 6/1993 | Guire et al. | 427/2 |
| 5,219,527 | 6/1993 | Hai et al. | 427/2 |
| 5,248,709 | 9/1993 | Brehm | 427/221 |

FOREIGN PATENT DOCUMENTS

| | | |
|---|---|---|
| 1212058 | 9/1930 | Canada . |
| 0071704 | 12/1986 | European Pat. Off. . |
| 2016729 | 10/1970 | Fed. Rep. of Germany . |
| 1274869 | 5/1972 | United Kingdom . |
| 1276006 | 6/1972 | United Kingdom . |

*Primary Examiner*—Shrive Beck
*Assistant Examiner*—Diana Dudash

[57] ABSTRACT

What is disclosed is a method for preparing carrier systems, adaptable to the covalent bonding thereto of biologically active materials, consisting of a known solid support material having a surface coated with a polymer containing functional groups suitable for covalent bonding, by coating the support material with a film-forming polymer dispersion and a non-film-forming polymer dispersion, suitably in admixture, at least one of the two polymer dispersions containing a polymer having functional groups suitable for covalent bonding with a biologically active material.

21 Claims, No Drawings

METHOD FOR MAKING CARRIER SYSTEMS FOR BIOLOGICALLY ACTIVE MATERIALS

This application is a continuation of application No. 07/745,155, now abandoned, filed Aug. 15, 1991.

The present invention relates to a method for making a carrier system for biologically active materials which are covalently bound to the polymer-coated surface of the carrier material and to a method for bonding a biologically active material to such a carrier system.

State of the Art

European patent publication 0,071,704 describes "High Surface Area Systems for Fixation of Substrates Containing Nucleophilic Groups". The reactive entities for bonding of the substrate containing the nucleophilic systems are part of a polymer latex prepared by emulsion polymerization, which latex consists of latex particles having a particle size of 0.03 to 6 microns, and wherein the latex itself is aggregated to form a system of high surface area and/or is fixed onto a carrier material of high surface area.

To the extent that bonding of the individual latex particles to one another does not occur because of film formation, their linkage to one another or to a carrier can, according to this document, take place by covalent bonding. Optionally, the covalent linking of the latex particles can also be strengthened by the use of multi-functional nucleophiles. Also the addition of minor amounts of a soft, film forming substance, e.g. latex particles having a lower glass transition temperature, is mentioned. Precipitation using the biologically active entities which are to be fixed, themselves, is especially preferred. In the aforementioned European document, the functional groups X are exactly defined as components of monomers $Z'-(R_n)-X$, wherein the groups X are able to react covalently, in a physiologically meaningful pH-region (about pH 5.0–9.0), at temperatures below 40° C., and in an aqueous medium, with the nucleophilic groups, especially amino, hydroxy, and thio groups of the biologically active materials which are to be fixed.

German patent document DE-A 20 16 729 provides a method for making insoluble enzymes in active form in which a copolymer is treated with an enzyme solution and a crosslinking of the enzyme-polymer complex and/or a neutralization of the residual reactive chemical groups is carried out. The teaching of this publication includes the destruction of any particle structure —if present from manufacture—by solution of the copolymer in solvents. In this way the requirement for the presence of a particle structure at film formation is eliminated. To the extent insoluble sediments or precipitates are the subject of the teachings, they are not the direct results of the polymerization process, but products resulting from a (external) crosslinking of the polymeric material formed, which reduces their accessibility all the more.

The state of the art pertinent to the immobilization of biologically active materials on polymeric carriers is treated in not a few review articles (cf. *Encyclopedia of Polymer Science and Engineering*, vol. 2, pp. 55–59, John Wiley 1985; *Characterization of Immobilized Biocatalysts*, Ed. K. Buchholz, Dechema-Monographs No. 1724-1731, vol 84, Verlag Chemie 1984; *Methods in Enzymology*, Ed. W. B. Jokoby, vol. 104, pp. 3–369, Academic Press 1984; *Biotechnology*, Ed. H. J. Rehm & G. Reed, vol. 7a, pp. 347–464, Verlag Chemie 1987.)

Problem and Solution

The last-mentioned literature citation points out that despite the large number of techniques for immobilization, no specific technique can claim to be universally useful to give an ideal result. If the immobilization leads to entrapment of the biologically active unit within the carrier matrix, then difficult accessibility for the substrates must be reckoned with because of the diffusion resistance, an effect which, among others, clearly influences the (apparent) Michaelis constant. Thus, classical entrapment is effectively limited to low molecular weight substrates and products, in which resistance to mass transport is held within limits. Internal diffusion effects understandably play a decisive role when dealing with an enzyme fixed in the interior of a porous carrier system.

In Biotechnology, (loc.cit. p. 353), the advantages and disadvantages of porous and non-porous carriers are compared. In non-porous carriers, the advantage of minimal limitations imposed by diffusion are weighed against the disadvantage of the small active surface and the resultant small enzyme loading, the need to use small carrier particles, and difficulties in obtaining them, particularly for continuous operations. For porous carriers, the large interior surface and high enzyme loading and the relative protection from damage from external effects are positive, but opposed thereto are the diffusion problems associated with the large interior surface, the high costs which, inter alia, unavoidably involve the control of the cavity dimensions, and possible liquid pressure problems connected with the tendency to gel formation.

Ideally, the biologically active structures should be fixed on a carrier having the greatest possible surface in such a way that the fewest possible biologically active structures are excluded from interchange with the substrate or that the optimum possibilities for access exist for the substrate molecules.

The solution in the aforementioned European patent represent an approach to this ideal, in so far as carriers having a large surface and which have the bonding functions for the fixation of biologically active materials, particularly enzymes, antibodies, etc., are made available. An interesting solution is likewise given in U.S. No. 4,710,525, which describes redispersible polymer latices having a core-shell structure wherein the functional groups for covalent fixation of the biologically active materials are in the shell.

These still leave disregarded the problem of making available efficient polymeric carrier systems for the covalent fixation of biologically active materials which assure the optimum possible utilization of the biologically active materials, which are as a rule expensive. Thus, the present invention pertains to a method for making carrier systems for the covalent bonding of biologically active materials, which systems have polymer-coated surfaces wherein the polymer contains the functional groups suitable for covalent bonding and wherein a support material, known per se, is coated with a mixture of a film forming polymer dispersion and of a non-film-forming polymer dispersion.

The Support Material

The carriers developed according to the state of the art are suitable as support materials. (Cf. *Biotechnology*, vol. 7a, loc. cit., pp 351–367, 411–412; Dechema Monographs, vol. 84, loc. cit., pp. 49–72.) Both inorganic as well as organic support materials are suitable. The following can be mentioned as carriers of inorganic origin: aluminum oxide; zirconium dioxide; magnesia; silicon dioxide; glass; minerals in various modifications, e.g. clays such as attapulgite, bentonite, kieselguhr, pumice, etc; ceramic materials; sand; titanium dioxide; and metals such as ferromagnetic materials; in both grafted and ungrafted condition. Further, organic carrier materials of natural origin are significant, such as polysaccharides (celluloses, dextrans, starches, agar, agarose, alginates, carrageenins, chitin, chitosan), as well as proteins such as collagen, gelatin, albumin, silk, inter alia, as well as various modifications of carbon.

Polystyrene, polyacrylates and -amides, maleic acid anhydride-polymers, vinyl- and allyl-polymers, and polyamides are mentioned as synthetic polymeric carriers.

Certain preferences for the geometry of the carrier have developed in the technology. For example, readily available spheres, with a diameter of about 1–10 mm, particularly around 6 mm, are mentioned.

In this regard, polystyrene spheres are particularly preferred.

However, in the sense of the present invention, coated surfaces must be considered to include those of bodies which are non-spherical and which do not have a strictly uniform shape, e.g. the surfaces of granules, sticks, as well as—because of their high surface area—bodies developed as carriers for catalysts, e.g. having a honeycomb structure, likewise the surfaces of containers, for example glass surfaces. Also, planar forms, comprising cellulose, e.g. coated papers, or, too, textiles such as silk.

In general, the established support materials satisfy the condition that they be chemically inert (or in plain meaning, activatable) under the conditions of fixation. When used for diagnostic purposes, it is recommended, too, for the present invention, to use beads or spheres having a diameter from about 0.01 to 10 mm, preferably the bead region from 0.1–0.6 mm, as well as the sizes from 0.01–10 mm, particularly the range of 6–7 mm, already used diagnostically. Calculated on area, surfaces of the carriers should have from 0.03 mm$^2$ to 100 cm$^2$, preferably 10 mm$^2$ to 10 cm$^2$, available. With planar carriers, one can use square or rectangular forms, but round forms can also be used, e.g. the known filter disks. Irregular forms are also possible.

A requirement which the carrier materials to be used according to the invention has in common with those of the state of the art is mechanical stability, particularly under shear stress. The materials should have sufficient stability for the usual manipulations such as filtration, stirring, and shaking, as well as during transport and in storage, and should not develop any disruptive dust from abrasion.

The Polymer Dispersions

The polymer dispersions, and to be sure the non-film-forming dispersion as well as the film forming dispersion, can be obtained in a known manner according to the rules of emulsion polymerization. (Cf. H. Rauch-Puntigam, Th. Völker, *Acryl- und Methacrylverbindungen,* pp. 217–230, Springer Verlag 1967; Houben-Weyl, *Methoden der orqanischen Chemic,* 4th ed., vol. 14/1, pp. 133–390, Georg Thieme Verlag 1961.) The polymerization can be carried out, for example, in imitation of German patent publications DE-OS 18 04 159, DE-OS 19 10 488, and DE-OS 19 10 532. The desired size of the latex particles is controlled in practice by the concentration of emulsifier at the onset of the emulsion polymerization. In general, the emulsifier concentration at the beginning of the emulsion polymerization is between 0.005 and 0.5 weight percent, based on the total polymerization batch. It is also possible to control the desired particle size by the addition of a defined amount of a finely divided seed latex. The size of the latex particles should be between 0.03 and 6 microns, preferably between 0.03 and 1 micron. The known anionic and nonionic emulsifiers can be used, for example fatty alcohol sulfates and -sulfonates, -phosphates, and -phosphonates, alkali metal salts of long chain fatty acids, and long chain sarcosides, as well as oxethylated fatty alcohols, substituted phenols which can in part be sulfated, as well as others emulsifiers used in emulsion polymerization (Houben-Weyl, *Methoden der organischen Chemie,* vol. XIV/1, loc.cit.).

The use of cationic surface active agents is recommended only if these are derived from tertiary or quaternary ammonium salts. Further, emulsifiers which can be polymerized into the polymer can be used.

As initiators, those generally common in emulsion polymerization can be used (cf. J. Brandrup, E. H. Immergut, *Polymer Handbook,* 2d ed., J. Wiley & Sons; H. Rauch-Puntigam, Th. Völker, *Acryl- und Methacrylverbindungen,* Springer Verlag 1967). Mentioned are peroxides, hydroperoxides, per-acids, and azo compounds, e.g. potassium peroxydisulfate and hydrogen peroxide, inter alia. As a rule the concentration of the initiators is in the conventional range, for example from 0.01 to 1.0 weight percent, based on the monomers. The solids content of the dispersions can be between 10 and 60 weight percent, according to the particle size.

The polymer dispersions to be used according to the invention can be composed of known monomers capable of emulsion polymerization. For examples, polymers comprising acrylates or methacrylates styrene and styrene derivatives vinyl fatty acid esters such as vinyl acetate and vinyl propionate vinyl halogen compounds such as vinyl chloride and tetrafluoroethylene vinylidene compounds as well as copolymers such as copolymers of styrene and butadiene, polyvinylidene copolymers with vinyl acetate, inter alia. In general, polymerization is free-radically initiated.

The molecular weight of the polymer (determination by gel permeation chromatography; cf. *Encyclopedia of Polymer Science & Engineering,* Bikales, Overberger, and Menges, 2d ed., vol. 10, pp 1–19, J. Wiley 1987) has not really proved to be critical.

From a practical viewpoint, the molecular weight of the polymers are in the range from 10,000 to $2(10^6)$, preferably above 50,000.

A necessary part of at least one the polymer types used is a minimum of functional groups X which are suitable for bonding with the biologically active material. The functional units X are preferably part of the non-film-forming dispersions. There can be an activatable group (group X') which requires an additional activating reagent Q, but the functional group X preferably is suitable for direct reaction with nucleophilic groups of the biologically active material, suitably under conditions which are biologically acceptable, i.e. which do not impair the ultimate effect of the biological activity. Conditions of this kind are, for example, a physiologically significant pH region of the aqueous medium, for example the pH range from 5.0–9.0, particularly buffer solutions, as well as the absence of agents which impair biological activity, and a suitable temperature which avoids the inactivation of proteins, e.g. one below 60° C., particularly below 40° C.

For example, carbonyl groups present on carrier T can be covalently linked to amino groups of the biologically active material analogously to the methods of peptide synthesis, for example with the carbodiimide method. Amide functions can be activated with glutaraldehyde or by hydrazinolysis and diazotization, which latter can also be used with esters. Aromatic amino groups on the carrier can also be activated by diazotization. Aliphatic amino groups can, for example, be covalently linked with amino groups of the biologically active material using glutaraldehyde, with D-cyclopenta-dialdo-1,4-furanose, or using thiophosgene.

Reaction with halogenated triazines or with 1,1'-carbonyldiimidazole is suitable for the activation of hydroxy groups, and, with glycol configurations, reaction with bromcyan to form imidocarbonate (cf. *Biotechnology*, Ed. H. J. Rehm & Reed, vol. 7a, loc.cit.).

As already mentioned, group X preferably is an activated group suitable for direct reaction with nucleophilic groups of the biologically active material.

Thus, X preferably signifies a group which is a sulfonic acid halide, a thioisocyanate, an activated ester, a thiocarbonyldioxy, a carbonylimidoyldioxy, a haloethoxy, a haloacetoxy, an oxirane, an aziridine, a formyl, a keto, an acryloyl, or an anhydride group.

As sulfonic acid halides, the chlorides and bromides come under consideration; the fluoro, chloro, and bromo compounds as haloacetoxy materials; as ester components of activated esters, those of hydroxylamino compounds such as N-hydroxy succinimide or N-hydroxy phthalimide, of phenols activated with electron-attracting groups, such as halophenols like trichlorophenol, nitrophenols, and of heterocyclic lactams such as pyridone.

Oxirane, keto, formyl, sulfonic acid chloride, and thioisocyanate groups, are particularly preferred, as well as activated carboxylic acid ester and carboxylic acid anhydride groups.

Monomers having the functional groups preferably correspond to the formula

Z - (R)$_n$- X wherein

X has the meaning given above,

R stands for a chemically inert spacer group between the functional group and the polymerizable entity, n is 0 or 1, and Z stands for a unit capable of being polymerized.

The size and type of the spacer, R, are comparatively uncritical. Typical representatives of this kind of spacers are, for example, $C_1$-$C_{20}$-, preferably $C_2$-$C_{12}$-, alkylene groups, wherein, optionally, carbon atoms can be replaced by ether bridges, or wherein there also can be alkyl branches and/or substitution, e.g. with an hydroxy function. However, R is preferably linear. Additionally, other original (i.e. before incorporation into the polymer) units containing bifunctional groups can result in a linkage both at the "polymer end" and at the "functional end" by way of amide, ester, ether, thioether, urea, urethane, sulfonamide, and similar groups. In general, the spacer distances the functional group X from the main polymer chain by 0.5–4 nanometers. In many examples, group R can be entirely absent, i.e. n can have the value 0.

Free-radically polymerizable entities are, e.g., vinyl groups, in which Z may, for example, signify

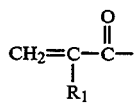

wherein $R_1$ stands for hydrogen or methyl or for —CH$_2$—COOR$_2$, —CH$_2$—CONHR$_2$, or —CH$_2$—CON(R$_2$)$_2$, wherein $R_2$ is an alkyl group having 1 to 4 carbon atoms.

Further, Z can derive from maleic acid:

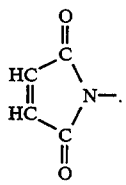

Also, maleic acid anhydride and itaconic acid anhydride are entities which are capable of reaction and at the same time are polymerizable.

For clarification of the formula Z - R - X, the following examples are given:

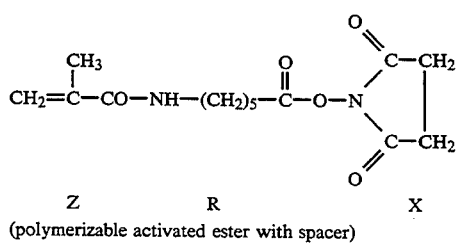

(polymerizable activated ester with spacer)

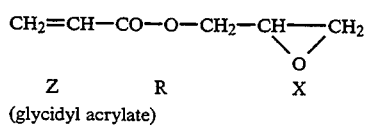

(glycidyl acrylate)

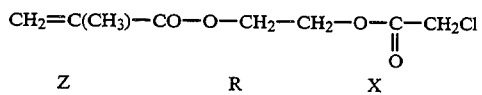
[2-(chloroacetoxy)-ethyl methacrylate]
(with labels Z, R, X)

CH$_2$=C(CH$_3$)—CO—O—C$_6$H$_2$Cl$_3$
(2,4,5-trichlorophenyl methacrylate) (R = O)

CH$_2$=C(CH$_3$)—CO—O—CH$_2$—CH$_2$—Br
(2-bromoethyl methacrylate)

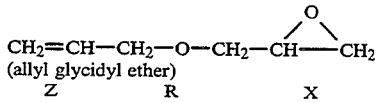
(allyl glycidyl ether)
(with labels Z, R, X)

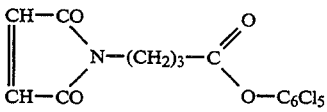
(addition product of methacrylic acid to 1,4-butanedioldiglycidyl ether)

CH$_2$=CH—COO—CH$_2$—CH$_2$—O—CSNH—(CH$_2$)$_6$—N=C=S
(addition product of acrylic acid-2-hydroxyethyl ester to 1,6-hexanediisothiocyanate)
(with labels Z, R, X)

CH$_2$=CH—O—CO—CH$_2$—Cl
(chloroacetic acid vinyl ester)

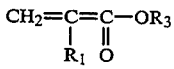
(4-maleimido-butyric acid pentachlorophenyl ester)
(with labels Z, R, X)

CH$_2$=C(CH$_3$)—COO—C$_6$H$_4$—SO$_2$—CH$_3$
(4-methylsulfinyl-phenyl methacrylate)

CH$_2$=CH—COO—CH$_2$—C≡CH
(propargyl acrylate)

Dispersions of the Polyacrylate Type

Polymer dispersions of the acrylate type are, as a rule, built up from (meth)acrylate monomers of the formula $$CH_2=C=C—OR_3$$
$$\phantom{CH_2=}|\phantom{=}\|$$
$$\phantom{CH_2=}R_1\phantom{=}O$$

wherein R$_1$ has the meaning designated earlier herein and wherein R$_3$ stands for an optionally branched alkyl group having 1–18 carbon atoms, particularly 1–8 C-atoms, or for a cycloalkyl group having 3 to 12 ring members, but especially a methyl, ethyl, propyl, butyl, and, above all, an n-butyl or a 2-ethylhexyl group. (Cf. H. Rauch-Puntigam, *Acryl- und Methacrylverbindungen*, Springer Verlag 1967, pp. 217–230.)

Essentially, hydrophobic monomers which come into consideration are, inter alia, dienes such as butadiene, chloropropene, and isoprene. Also, activated vinyl compounds such as vinyl esters of fatty acids like vinyl acetate and vinyl propionate; vinyl ethers; allyl ethers and allyl esters; acrolein; vinylmethyl ketone; heterocycles containing vinyl groups, such as vinylimidazole, vinylpyrrolidine, vinylpyridine, and vinylcarbazole; and styrene and its derivatives, particularly alkylated derivatives such as α-methylstyrene and vinyltoluene, inter alia, can be polymerized, in which case, however, attention must be paid to the fact that the copolymers can enter into (undesirable) reciprocal reactions, determined by their groups, with the biologically active materials to be fixed. In certain cases this can be appropriate from the viewpoint of a possible hapten effect, for example, entirely apart from the use of monomers containing aromatics.

In general, the amount of the (meth)acrylate type monomers mentioned above preponderates in the polymers forming the two acrylate-type dispersions. As a rule, their content amounts to over 50 weight percent and—to the extent they are nonfunctionalized polymer components—up to 99.9 weight percent, preferably up to 99 weight percent.

At least one of the two dispersions contains the monomers described earlier having functional groups X or activatable groups X'. The amount of monomers having functional groups X in the polymers of the two dispersions can be 0.1 to 80 weight percent. In general, the amount of the (meth)acrylate monomers of the above formula is 1 to 40 weight percent.

Besides the functionalized monomers, the polymers can contain still other comonomers, e.g. clearly hydrophilic monomers, especially of the formula

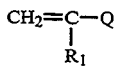

wherein R$_1$ has the meaning earlier ascribed and Q stands for the groups —CN, —COOR$_4$ wherein R$_4$ is hydrogen, sodium, potassium, or ammonium, or Q stands for

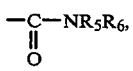

wherein $R_5$ and $R_6$ stand for hydrogen or for an alkyl group corresponding to $R_3$, or, together with the nitrogen atom, optionally with the inclusion of still further nitrogen or oxygen atoms, form a 5- or 6- membered heterocycle, or stand for an optionally branched alkyl group having 2 to 8 carbon atoms which has at least one, preferably terminal, —OH or —NR$_5$R$_6$ groups having the meaning given above.

If they are present at all, the amount of hydrophilic monomers in the polymers, which may bring with them improved adherence and improved suitability for specialized uses, is from 0.5 to 30 weight percent, preferably from 1 to 20 weight percent (based on the monomers employed).

In addition to the monomer components described above, the polymers may also contain crosslinking monomers. By "crosslinking monomers" is to be understood, as usual, monomers containing two or more reactive double bonds in the molecule, for example diols or polyols esterified with acrylic acid or, preferably, methacrylic acid, as well as allyl compounds like allyl methacrylate, and triallylcyanurate, inter alia.

As examples, ethylene glycol dimethacrylate, 1,4-butanediol dimethacrylate, triglycol dimethacrylate, and trimethylolpropane trimethacrylate are mentioned.

The amount of crosslinker is as a rule between 0 and 50 weight percent, preferably 2 to 20 and especially 5–20 weight percent, based on the totality of monomers.

The polymer content of the dispersions is, as a rule, from 10 to 60 weight percent.

Dispersions of the Polystyrene Type

The preparation of styrene dispersions is extensively described in Houben-Weyl, *Methoden der organischen Chemie*, 4th ed., vol XIV/1, Georg Thieme Verlag 1961, pp. 834–839. Fatty soaps such as sodium oleate, resin soaps and alkyl sulfonates, and cationic emulsifiers are particularly suitable as emulsifiers, normally in amounts from 2 to 6 weight percent based on the amount of water.

As initiators, here, too, water soluble materials above all are used, e.g. like the peroxydisulfate salts, but also redox systems, usually in amounts from 0.01 to 0.2 weight percent, based on the monomers. As chain transfer agents, those commonly used, e.g. the sulfur regulators, can be employed, normally in amounts from 0.05 to 2 weight percent, based on the monomers.

For initiation of the reaction using peroxydisulfates, a weakly acid medium (pH 3–6) is advantageously chosen. Advantageously, care is taken to exclude atmospheric oxygen during the polymerization, e.g. by working under an inert gas such as nitrogen.

As comonomers for styrene or the known free radically polymerizable styrene derivatives, the monomers mentioned under the heading "Dispersions of the Acrylate Type" can be used, whereby, analogously, the roles of the (meth)acrylate monomers are taken over by styrene and/or its derivatives and vice versa.

Thus, in general, the amount of styrene or styrene derivatives in the polymers is more than 50 weight percent and up to 100 weight percent Copolymers of the styrene-butadiene type are also of particular interest. In the styrene-butadiene type, starting from a 1:1 ratio by weight, the property spectrum can be shifted in the direction of being "harder" (higher styrene amount) or "softer". (Cf., e.g., Houben-Weyl, 4th ed., loc.cit., vol. XIV/1, pp. 147, 327.)

Dispersions of the Polyvinyl Fatty Acid Ester Type

As monomers of this type are such having the formula

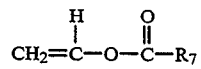

wherein $R_7$ stands for an alkyl group having 1 to 6 carbon atoms, particularly 1 to 2 carbon atoms, i.e. vinyl acetate and vinyl propionate.

Comonomers, for example, are optionally halogenated olefins such as ethylene, vinyl chloride, other vinyl esters such as vinyl phosphonic acid diester, (meth)acrylates of the kind already mentioned (cf. "Dispersions of the Polyacrylate Type"), and (meth)acrylonitrile, inter alia. (Cf. Houben-Weyl, loc. cit., 4th ed., vol. 14/2, p. 704, vol. 14/1, pp. 911–918.) The polymerization in general follows the method already described, for instance with reference to the emulsifiers, initiators, and chain transfer agents. Polymerization is advantageously in the pH region 4–5.

Polyvinylidene copolymers are of special interest.

Dispersions of the Polyvinylhalide Type

Vinyl chloride and particularly vinylidene chloride are, above all, monomers of this kind (Houben-Weyl, loc. cit., pp. 887, 891–905). As acrylate components, acrylic acid methyl ester, -ethyl ester, -butyl ester, -octyl ester, -nonyl ester, - 2-ethylhexyl ester, and -3,5,5-trimethylhexyl ester are named, as well as methacrylic acid methyl ester and methacrylic acid amide. In general, for copolymers of vinylidene, the amount of comonomers of the acrylate type and/or of (meth)acrylonitrile, or vinyl esters (or vinyl chloride) is 10–20 weight percent, in which case the softening temperature usually decreases to a desired value.

Polymerization of the halogenated vinyl compounds also follows the methodology already described. Alkali metal salts of fatty acids or allyl- or acryl-sulfonates and nonionic polyethyleneoxide emulsifiers are particularly usable as emulsifiers. As initiators, the ordinary per compounds, particularly redox initiators, are suitable.

The Film-Forming Dispersion

The film-forming dispersion is characterized in that, in the course of drying, i.e. during evaporation of the liquid medium, as a rule an aqueous medium, the glass transition temperature $T_g$ is exceeded.

The glass transition temperature $T_g$ is, as a first approximation, the same as the glass transition temperature of the dried polymer, providing that the polymer shows no hydroplastic behavior, i.e. is not plasticized by water as a result of its composition.

The glass transition temperature $T_g$ can be derived from the contributions of the monomers. [Cf. R. Vieweg, F. Esser, *Kunststoff Handbuch*, vol. IX, Polymethacrylate, pp. 333–342, Carl Hanser Verlag 1975; H. F. Mark et al., Ed., *Encyclopedia of Polymer Science and Technology*, vol. 7, pp. 531, 534, John Wiley 1987; T. G. Fox, Bull Am. Phys. Soc. 1, 123 1956.]

However, knowledge of the minimum film-forming temperature (MFT) is generally sufficient for selecting suitable polymer dispersions of the monomers contained therein. In agreement with the knowledge of the man skilled in the art (according to which the MFT is the decisive characteristic measure of the tendency of a polymer dispersion to form films, the value of which, in degrees Centigrade, must be exceeded during drying), the MFT of the film-forming dispersion is to be set below 60° C., preferably less than 40° C., particularly less than 30° C.

Determination of the MFT is according to DIN 35 787. Film-forming dispersions comprising (meth)acrylate dispersions which meet the conditions described above are particularly preferred. (Cf. Houben-Weyl, 4th ed., vol. XIV/1, loc.cit., p.1048.)

The film-forming dispersion can be chosen from among the polymer classes discussed above, providing that the polymer satisfies the rules set out above. In practice, the glass transition temperature $T_g$ of the polymers does not exceed the value of 30° C., i.e. relatively "soft" polymers are involved. (Values for the glass transition temperature are found, for example, in Brandrup-Immergut, *Polymer Handbook*, 2d ed, J. Wiley.) By the copolymerization of corresponding monomers, a wide spectrum of latices with continuously gradated film hardnesses can be prepared. Dispersions of the following composition are especially mentioned: Methacrylic acid esters of $C_1$-$C_4$- alcohols, particularly methyl methacrylate, in amounts from 20 to 80 weight percent, especially 20-60 weight percent, as well as acrylic acid esters of $C_1$-$C_4$- alcohols in amounts from 80 to 20 weight percent, based on the totality of the polymer.

The Non-Film-Forming Dispersion

The aqueous non-film-forming dispersion has the fundamental property that the freezing point of the polymer is above the film-forming temperature. In the common idiom, one can designate the polymer of the non-film-forming dispersion as "hard". A requisite therefor is the predominance of so-called "hard" monomers, recognizable from the softening points of their homopolymers (cf. Houben-Weyl, 4th ed., loc.cit., vol. XIV/1, pp. 1034). Polymethacrylic acid esters are known to be "harder" than polyacrylic acid esters. The "hardness" at first decreases with increasing size of the alcohol group and then increases after n-dodecyl in the methacrylate ester series and after the n-octyl ester in the acrylate ester series. Methyl methacrylate and styrene and its derivatives, for example, are "hard" monomers.

Alternatively to the use of "hard" monomers, of the kind like methyl methacrylate or styrene and its derivatives, the non-film-forming dispersion can also be so made up such that intrinsically "soft" monomers are combined with larger amounts of crosslinking monomers, for examples with at least 5 weight percent and up to 50 weight percent. Such polymers do not form closed films.

Preferably the non-film-forming dispersions are polymers with more than 60 weight percent of "hard" monomers such as methyl methacrylate or styrene and its derivatives. The polymer content in the dispersions is, as a rule, in the range of 10 to 60 weight percent.

The non-film-forming dispersion generally exhibits particles sizes in the range from 0.03 to 5 microns, preferably 0.1 to 2 microns.

The film-forming dispersion in general has particle sizes in the range from 0.02 to 5 microns, preferably 0.04 to 0.5 microns. Determination of the particle size is done with the "Nano-Sizer TDM" of the firm of Coulter Electronics Ltd., Luton, Bedfordshire, England. As a practical rule of measurement, it can be said that the particles of the non-film-forming dispersion at any given time should on average be larger by a factor of 1.2 to 20 than those of the film-forming dispersion, preferably 1.5 to 10 times, and especially 2 to 5 times, larger.

The quantitative ratio of the two kinds of dispersions when used according to the invention is advantageously at 50:50 by weight up to 99 parts by weight (pbw) of non-film-forming dispersion to 1 pbw of film-forming dispersion, in particular from 60 pbw to 40 pbw up to 95 pbw to 5 pbw, and especially from 65 pbw of non-film-forming dispersion to 35 pbw of film-forming dispersion up to 90 pbw to 10 pbw, based on the dry polymer. From this can be derived the following surprising finding: The values derived from theoretical considerations for a meaningful upper limit on the film-forming polymer component in the mixtures is about 26 volume percent. (As a first approximation, volume percent and weight percent can be equated for the present consideration.)

As the difference in particle sizes increases, it is to be expected that the real, existing, system approaches the ideal form of close spherical packing of the non-film-forming particles, with the film-forming particles are in the interstices. Thus, it could be concluded that with an increase in the particle size ratio, the film-forming component is to be reduced below the acceptable theoretical limit of 26 volume percent in order to form a porous material or to avoid the complete filling of the geometrically possible voids. Factually it has proved, however, that the above mentioned value of about 26 volume percent of film-forming polymer can be drastically exceeded without appearance of the exclusion effect, presumably because the real, existing, system significantly departs from close spherical packing.

Preparation of the Carrier System

Preparation of the carrier systems for covalent binding of biologically active material according to the invention takes place by coating of the support material with a mixture of the film-forming polymer dispersion and of the non-film-forming polymer dispersion, preferably in the aforementioned ratios. Coating can be accomplished in a known manner, e.g. by spraying or immersion, preferably using a mixture, but individual application (e.g. sequential spraying) is also possible.

For example, application of the dispersion mixture using a spray apparatus has proved valuable. A particularly good embodiment provides for the spraying of the dispersion mixture onto beads or spherically formed support material (see the section on support material), advantageously in a coating drum with the simultaneous addition of air.

The coating of smaller particles requires a particularly intensive drying so that adhesion of the particles is avoided. Special apparatus having a high throughput of air is suitable for this purpose, e.g. fluidized bed apparatus or coating apparatus having perforated drums.

The method parameters for the coating process, e.g. spray rate, amount of air, and inlet air parameters, must be adapted to the properties of the core material and of the dispersion mixture.

Proceeding from a definition of a "layer" as "the thickness of a monolayer", the following measurement limits have proved themselves: about one layer to 1000 layers, preferably one layer to 100 layers.

As a rule of thumb, one can also use the ratio of the support body and the coating, according to which a ratio by weight of support material to coating (in the dried state) from 1:50 to 10,000:1 leads to useful results.

The biologically active material

The biologically active materials, the fixation of which to solid carriers is carried out for a variety of purposes in science and technology, fall into many different classes. Thus, for example, a classification from a chemical standpoint is possible, e.g. according to functional groups such as amino acids, peptides and proteins, as nucleosides, nucleotides and polynucleotides (saccharides), whereby—as is again evident—low molecular weight and high molecular weight kinds of compounds are to be differentiated.

Polymeric materials demand special interest, primarily proteins, lipoproteins, polysaccharides, (mucopolysaccharides) nucleic acids such as DNA and RNA, and lipoids.

In many cases, the choice of available fixation mechanisms, e.g. covalent, polar (ionic), complex chemical, hydrophobic, or by occlusion, is also determined by the kind of functional groups. Further, a classification according to biological activity is meaningful: According to this, for example, biocatalyts such as enzyme complexes, blood factors, hormones (messenger substances), and immunologically active materials such as antigens and antibodies (e.g. monoclonal antibodies), are differentiated. Further, fixation can be according to morphologically (and mostly also functionally) definable entities, e.g. as organelles like mitochondria, viruses, whole cells and cell components, and cell hybrids such as bacterial cells, eukaryotic cells, inter alia. Finally, a classification of the immobilized material according to the intended technical use offers itself. Thus, for example, in addition to the use of biocatalysts, their use in diagnosis and in (affinity) chromatography is of interest.

The systems according to the invention are also outstandingly adaptable for use in "cell sorting" and in depletion therapy. In this case, one suitably proceeds using a modification in which, for example, a monoclonal antibody or another ligand which is specific for the "receptor site" in question is used.

The immobilized biocatalysts can be used, for example, for the production or reaction of very diverse substrates such as amino acids, peptides and enzymes, sugars, organic acids, antibiotics, steroids, nucleosides and nucleotides, lipids, terpenoids, and basic organic chemicals (cf. Ullmann, 5th ed., vol. 9A, loc.cit., pp. 389-390).

As immunologically active materials, the following are mentioned as exemplary: microorganisms such as gram-positive and gram-negative bacteria, spirochetes, mycoplasma, mycobacteria, vibrions, actinomycetes, protozoa such as intestinal protozoa, amoebas, flagellates, sporozoa, intestinal nematodes and tissue nematodes (worms), trematodes (schistosomes, leeches), cestodes, toxoplasma; also fungi such as sporotrichum, cryptococcus, blastomyces, histoplasma, coccidioides, candida; viruses and rickettsia such as canine hepatitis, Shope papillomas, influenza A+B, fowl plague, herpes simplex, HIV, adenoviruses, polyane, Rous sarcoma, smallpox, polio virus, measles, canine distemper, leukemia, mumps, Newcastle disease, Sendai, ECHO, hoof and mouth disease, psittacosis, rabies, ectromelia, and tree viruses; also tissue antigens; enzymes such as pancreatic chymotrypsinogen, procarboxypeptidase, glucose oxidase, lactate dehydrogenase, uricase, amino acid oxidase, urease, asparaginase, and protease; blood cell antigens; blood group substances, and other isoantigens such as blood platelets, leucocytes, plasma proteins, milk proteins, saliva proteins, and urine proteins; and antibodies inclusive of auto-antibodies. Monoclonal antibodies which are directed against antigens of the following kind, for example, are particularly mentioned:

| Antigen-Classes | Antigen |
|---|---|
| Bacterial | tetanus toxoid |
| | H. Influenza type b polysaccharide |
| | diphtheria toxin |
| | *chlamydia trachomatis* |
| | *M. leprae* |
| | lipopolysaccharide/endotoxin |
| | *pneumococci* |
| | LPS of *P. aeruginosa* |
| | exotoxin of *P. aeruginosa* |
| | *streptococci* group A carbohydrate |
| Viral | X31 influenza virus nucleoprotein |
| | measles virus |
| | HSV glycoprotein D |
| | measles virus, *nucleocapsid* |
| | *cytomegalia* virus |
| | influenza A virus |
| | German measles virus antigen |
| | HTLV I |
| | *varicella zoster* |
| | HBsAg |
| Autoimmune | double-stranded DNA |
| | islet cells (*diabetes mellitus*) |
| | *myasthenia gravis*, antiidiotypes |
| | thyrotropin receptors |
| | rheumatoid factors |
| | acetylcholine receptors |
| | thyroid gland |
| | sperm |
| Tumor | breast cancer |
| | prostatic cancer |
| | lung cancer |
| | stomach cancer |
| | melanoma |
| | BD2 (human melanoma) |
| | glioma |
| | rectal cancer |
| | leukemia |
| | cervical cancer |
| Tissue/blood | rhesus D |
| | blood group antigens |
| | HLA-A, B, C, DR |
| | intermediary filaments |
| Others | malaria |
| | Forssmann antigen |
| | sheep erythrocytes |
| | nitrophenol |
| | dinitrophenol |
| | trinitrophenol |
| | keyhole limpet hemocyanin (KLH) |
| | insulin. |

Immunoglobulins of all classes, especially of the oligomeric kind, and particularly IgM, IgE, and IgA, are especially mentioned.

The Fixation of Biologically Active Material -Covalent Fixation

The covalent fixation of biologically active materials presupposes the intactness of the reactive groups X in the polymers of the film-forming and non-film-forming dispersions and, also, a corresponding protective preparation and availability. Such a protective preparation is described, for example, in European patent publication EP-A 0 071 704.

The following examples are given by way of illustration.

EXAMPLES

Example 1 a) Preparation of a Seed Latex for Polymer Dispersions

Seed Latex A 2.90 g methyl methacrylate
2.90 g isobutyl methacrylate
0.30 g glycol dimethacrylate
3.60 g ammonium peroxydisulfate and
0.72 g sodium lauryl sulfate are added to 1482 g of doubly distilled water in a 2 liter polymerization vessel equipped with a reflux condenser, stirrer, and thermometer, and are heated to 80° C.

A mixture of
171.00 g methyl methacrylate
171.00 g isobutyl methacrylate and
18.00 g glycol dimethacrylate is added dropwise at 80° C. over 2 hours with stirring. Stirring is continued for another 2 hours at 80° C. The mixture is then cooled to room temperature and filtered. A dispersion is obtained which is essentially free of coagulate, has a solids content of about 20 weight percent, has a viscosity of 4 mPa s (determined according to DIN 53 018), and has an average particle radius of 120 nanometers (determined with a Coulter "Nanosizer").

b) Preparation of a Seed Latex for Polymer Dispersions

The initial batch is heated in a Witt jar to 80° C. with stirring, the initiator [ammonium peroxydisulfate or the sodium salt of 4,4-azobis-(4-cyanovalerianic acid)] is added, and then the feed is added as an emulsion or monomer mixture over a specified time. 15 minutes after termination of the feed, the dispersion is cooled to room temperature and filtered.

Seed Latex B

| Initial Batch: | 1478.0 g water |
| | 2.9 g isobutyl methacrylate |
| | 2.9 g methyl methacrylate |
| | 0.3 g glycol dimethacrylate and |
| | 3.6 g ammonium peroxydisulfate |
| Feed: (over 20 minutes) | 168.1 g isobutyl methacrylate |
| | 168.1 g methyl methacrylate and |
| | 17.7 g glycol dimethacrylate. |

Solids content: 21.1 weight percent; pH: 2.4; viscosity: 5 mPa s; particle diameter: 480 nanometers. Seed Latex C The method of Example 1b) is followed except that:

| Initial batch: | 1485.0 g water |
| | 0.72 g sodium lauryl sulfate and |
| | 3.6 g ammonium peroxydisulfate. |

Solids content: 21.4 weight percent; pH: 2.3; viscosity: 5 mPa s; particle diameter: 270 nanometers. Seed Latex D

| Initial Batch: | 427.0 g water |
| | 540.0 g seed latex B |

| | 9.0 g "Titrasol" solution pH 7 (Merck) and |
| | 0.35 g 4,4'-azobis-(4-cyanovalerianic acid) sodium salt |
| Feed: | 585.0 g water |
| | 0.88 g sodium lauryl sulfate |
| | 2.12 g 4,4'-azobis-(4-cyanovalerianic acid) sodium salt |
| | 119.7 g isobutyl methacrylate |
| | 119.7 g methyl methacrylate and |
| | 12.6 g glycol dimethacrylate. |

Solids content: 21.2 weight percent; pH: 6.2; viscosity: 5mPa s; particle diameter: 730 nanometers.

Example 2

Preparation of a Film-Forming Dispersion Having Epoxy Groups as Functional Groups X A solution consisting of
7.50 g phosphate buffer, pH: 7.0
0.29 g 4,4'-azobis-(4-cyanovalerianic acid) sodium salt
0.48 g sodium lauryl sulfate
150.00 g seed latex A of Example 1 and
275.00 g distilled water is prepared in a 2 liter polymerization vessel having a reflux condenser, stirrer, and thermometer, and heated to 80° C.

An emulsion consisting of
210.00 g ethyl acrylate
75.00 g methyl methacrylate
15.00 g glycidyl methacrylate
1.76 g 4,4'-azobis-(4-cyanovalerianic acid) sodium salt
0.73 g sodium lauryl sulfate and
933.00 g distilled water is added to this solution dropwise, with stirring, at 80° C. over 4 hours.

The dispersion is stirred for a further 15 minutes, cooled to room temperature, and filtered. A fully coagulate-free dispersion having a solids content of about 20 weight percent, a pH value of 7.0, a viscosity of 6 mPa s, and an average particle radius of about 240 nanometers is obtained.

Example 3

Preparation of a Non-Film Forming Aqueous Polymer Dispersion Having Epoxy Groups as Functional Groups X A mixture of
7.50 g phosphate buffer pH =7.0
0.29 g 4,4'-azobis-(4-cyanovalerianic acid) sodium salt
30.00 g Seed latex A of Example 1 and
340.00 g doubly distilled water is added to a polymerization vessel and warmed to 80° C.

An emulsion, prepared from
180.00 g methyl methacrylate
105.00 g ethyl acrylate
15.00 g glycidyl methacrylate
1.76 g 4,4'-azobis-(4-cyanovalerianic acid) sodium salt
0.73 g sodium lauryl sulfate and
865.00 g doubly distilled water, is added to this mixture over 4 hours at 80° C. The dispersion is stirred for a further 15 minutes at 80° C., then cooled to room temperature and filtered. A coagulate-free dispersion is obtained having a solids content of about 20 weight percent, a pH value of 7.0, a viscosity of 6 mPa s, and a particle radius of about 400 nanometers.

Example 4

Preparation of a Film-Forming Polymer Dispersion Having Epoxy Groups as Functional Groups X

| Initial Batch: | 272.0 g water |
| --- | --- |
| | 0.48 g sodium lauryl sulfate |
| | 7.5 g "Titrisol" solution pH 7 (Merck) |
| | 150.0 g Seed latex C and |
| | 0.29 g 4,4'-azobis-(4-cyanovalerianic acid) sodium salt |
| Feed: | 932.0 g water |
| (over 240 minutes) | 0.73 g sodium lauryl sulfate |
| | 1.76 g 4,4'-azobis-(4-cyanovalerianic acid) sodium salt |
| | 210.0 g ethyl acrylate |
| | 75.0 g methyl methacrylate and |
| | 15.0 g glycidyl methacrylate. |

Solids content: 20.2 weight percent; pH: 7.3; viscosity: 5 mPa s; particle diameter: 560 nanometers; MFT: 5° C.

Example 5

Preparation of a Non-Film-Forming Polymer Dispersion Having Functional Groups X Containing Epoxy Groups The feed consists of Emulsion 1 and Emulsion 2 in a ratio of 70:30 which are added one after the other.

| Initial Batch: | 407.0 g water |
| --- | --- |
| | 9.0 g "Titrisol" solution pH: 7 (Merck) |
| | 36.00 g seed latex C and |
| | 0.35 g 4,4'-azobis-(4-cyanovalerianic acid) sodium salt |
| Emulsion 1: | 726.0 g water |
| (over 168 minutes) | 0.61 g sodium lauryl sulfate |
| | 1.48 g 4,4'-azobis-(4-cyanovalerianic acid) sodium salt |
| | 163.8 g methyl methacrylate |
| | 75.6 g ethyl acrylate |
| | 12.6 g allyl methacrylate and |
| Emulsion 2 | 311.0 g water |
| (over 72 minutes) | 0.27 g lauryl sulfate |
| | 0.64 g 4,4'-azobis-(4-cyanovalerianic acid) sodium salt |
| | 64.8 g ethyl acrylate and |
| | 43.2 g glycidyl methacrylate |

Solids content: 20.8 weight percent; pH: 7.3; viscosity: 5 mPa s; particle diameter: 760 nanometers; MFT greater than 50° C.

Example 6

Preparation of a Film-Forming Polymer Dispersion

| Initial Batch: | 560.0 g water |
| --- | --- |
| | 1.12 g sodium lauryl sulfate |
| | 0.98 g 4,4'-azobis-(4-cyanovalerianic acid) sodium salt and |
| Feed: | 860.0 g water |
| (over 240 minutes) | 4.2 g sodium lauryl sulfate |
| | 0.98 g 4,4'-azobis-(4-cyanovalerianic acid) sodium salt |
| | 420.0 g ethyl acrylate and |
| | 180.0 g methyl methacrylate |

Solids content: 28.7 weight percent; pH: 6.7; viscosity: 6 mPa s; particle diameter: 82 nanometers; MFT: 8° C.

Example 7

Preparation of a Non-Film-Forming Polymer Dispersion

| Initial Batch: | 1411.0 g water |
| --- | --- |
| | 37.5 g "Titrisol" solution pH: 7 (Merck) |
| | 1200.0 g seed latex D and |
| | 1.18 g 4,4'-azobis-(4-cyanovalerianic acid) sodium salt |

After addition of the initiators, an emulsion consisting of

| Feed 1 | 1830.0 g water |
| --- | --- |
| | 2.92 g sodium lauryl sulfate |
| | 5.29 g 4,4'-azobis-(4-cyanovalerianic acid) sodium salt |
| | 313.5 g isobutyl methacrylate |
| | 313.5 g methyl methacrylate and |
| | 33.0 g glycol dimethacrylate | is first added dropwise over a period of 120 minutes and then, within 60 minutes are simultaneously added a) a monomer mixture of

| | 126.0 g glycidyl dimethacrylate |
| --- | --- |
| | 102.0 g methyl methacrylate and |
| | 12.0 g glycol dimethacrylate | and b) a solution of

| (Feed 2) | 601.1 g water |
| --- | --- |
| | 60.0 g methacrylamide and |
| | 1.777 g 4,4'-azobis-(4-cyanovalerianic acid) sodium salt. |

Solids content: 20.8 weight percent; pH: 7.7; viscosity: 5 mPa s; particle diameter: 1120 nanometers; MFT greater than 60° C.

Example 8

Preparation of a Non-Film-Forming Polymer Dispersion

The feed consists of an Emulsion 1 and an Emulsion 2 in a ratio of 4:1, added one after the other.

| Initial Batch | 559.0 g water |
| --- | --- |
| | 0.42 g sodium lauryl sulfate and |
| | 0.98 g 4,4'-azobis-(4-cyanovalerianic acid) sodium salt |
| Emulsion 1 | 679.0 g water |
| (over 192 minutes) | 3.36 g sodium lauryl sulfate |
| | 0.78 g 4,4'-azobis-(4-cyanovalerianic acid) sodium salt |
| | 456.0 g methyl methacrylate and |
| | 24.0 g allyl methacrylate |
| Emulsion 2 | 177.0 g water |
| (over 48 minutes) | 0.84 g sodium lauryl sulfate |
| | 0.2 g 4,4'-azobis-(4-cyanovalerianic acid) sodium salt |
| | 84.0 g ethyl acrylate and |
| | 36.0 g methyl methacrylate. |

Solids content: 29.6 weight percent; pH: 6.7; viscosity: 5 mPa s; particle diameter: 204 nanometers; MFT greater than 50° C.

Example 9

Preparation of a Film-Forming Polymer Dispersion

| Initial Batch: | 560.0 g water |
| --- | --- |
| | 1.12 g sodium lauryl sulfate and |
| | 0.98 g 4,4'-azobis-(4-cyanovalerianic acid) sodium salt |
| Feed: | 860.0 g water |
| (over 240 minutes) | 4.2 g sodium lauryl sulfate |
| | 0.98 4,4'-azobis-(4-cyanovalerianic acid) sodium salt |
| | 420.0 g ethyl acrylate and |
| | 180.0 g methyl methacrylate. |

Solids content: 28.7 weight percent; pH: 6.7; viscosity: 6 mPa s; particle diameter: 82 nanometers; MFT: 8° C.

Example 10

Preparation of a Film-Forming Polymer Dispersion 920 g water
29 g ethoxylated isononylphenol (degree of ethoxylation =100)
346 g ethyl acrylate
146 g methyl methacrylate and
6 g methacrylic acid are put in a Witt jar and the apparatus is rinsed with $N_2$. Polymerization is initiated by the addition of 0.5 g of ammonium peroxydisulfate, 0.7 g of sodium pyrosulfite, and 0.01 g of iron (II) sulfate. After passing a temperature peak, the batch is cooled to 40° C. and 100 g ethoxylated isononylphenol (as above)
346 g ethyl acrylate
146 g methyl methacrylate and
6 g methacrylic acid are added and the polymerization initiated anew by the addition of 0.7 g of sodium pyrosulfite and 0.5 g of ammonium peroxydisulfate. After passing a temperature maximum, the batch is cooled to room temperature and adjusted to pH 7.0 with NaOH and then diluted with water to a solids content of 30 weight percent. viscosity: 20 m Pas. NFT: 7° C. solids content: 30%; particle diameter: 160 nm viscosity: 20 m Pas. MFT: 7° C.

Example 11

Preparation of Mixtures of Film-Forming Dispersion and Non-Film-Forming Dispersions Suitable for Use Useful mixtures are obtained by mixing the polymer dispersions from Examples 2 and 3 in ratios (by weight percent) as given in following Tables 1-7.

34 ml of the dispersion mixtures are diluted to a final volume of 200 ml with deionized water.

Example 12

Coating of Polystyrene Beads with a Polymer Suspension a) The spray apparatus is filled with 6-8 ml of the mixtures from Example 11 which are to be used.

b) A coating kettle (diameter 145 mm, two divider plates) is provided with 150 polystyrene beads ("Spherotech" beads from Spherotech-Works GmbH, Fulda, Federal Republic of Germany) having a diameter of 6.35 mm. Rotation of the kettle is at 50-70 rpm and 5-7 ml of the useful mixture are sprayed on the spheres while they are in motion inside the coating kettle. The spraying process is carried out over about 30 minutes at room temperature, during which time an unheated stream of air is blown into the coating kettle to evaporate moisture.

c) On conclusion of the coating step, the coated beads are stored in a sealed polystyrene flask at −15° C. until they are used, e.g. for the immobilization of antibodies.

In an analogous manner, inorganic granulates such as of calcium carbonate, aluminum oxide, titanium dioxide, or silicon dioxide ("Aerosil") can be coated with comparable success.

Example 13

Immobilization of Monoclonal Antibodies on Polystyrene Beads Coated with the Non-Film-Forming and Film-Forming Dispersions a) 1000 micrograms of a mouse monoclonal antibody (directed against a human polypeptide hormone of molecular weight about 30,000) are dissolved in 20 ml of a 0.3 molar potassium phosphate buffer solution (pH: 8.0).

b) This antibody preparation is applied over 100 beads, coated according to Example 12, present in a glass beaker.

c) This mixture is let stand at 23° C. overnight without moving.

d) The aqueous portion of this mixture is removed by suction filtration and the remaining beads are washed three times with 80 ml portions of PBS (standard buffer with added NaCl, pH: 7.2). The wash procedure consists of gentle shaking for five minutes, followed by suction filtration of the aqueous phase, whereby the beads remain in the container used.

e) After the third washing, 20 ml of a buffer solution containing 1 weight percent of serum albumin in PBS (pH: 7.2) are added to the beads. This mixture is let stand overnight at 23° C. without shaking.

f) Washing follows, as described in b).

g) The loaded beads are stored in a refrigerator at +5° C. until use.

Example 14

Radio-Immunometric Determination of the Antigen (Human Polypeptide Hormone, Molecular Weight about 30,000)

a) The polystyrene spheres obtained according to Example 13 are put into test tubelets having hemispherical bottoms (9.6 mm diameter), one bead per reagent glass.

b) 100 microliters of a radioactive tracer (various monoclonal antibodies which are directed against the aforementioned antigen and which are marked with $^{125}I$ in the order of magnitude of 50,000 counts per minute) are added thereto.

c) Immediately after addition of the tracer, 100 microliters of the antigen are added in the concentrations given in the following Tables.

d) The mixture is shaken for 3 hours at room temperature (21° C.) at 300 rpm using an orbital shaking machine.

e) The aqueous portion of the incubation batch is removed by suction filtration.

f) Each reagent glass with its bead is washed three times with 1 ml portions of buffer solution (2 weight percent bovine serum albumin in 0.2 molar tris-buffer at pH 8.5 and 1.2 weight percent of "Tween 20" emulsifier).

g) The test tubelets are counted in a gamma scintillation counter ( "Multi Crystal Gamma Counter LB 2103"). The results obtained in this manner are given in following Tables 1-7.

Discussion of the Results

As the values in Tables 1-7 show, the coating of polystyrene spheres or beads with a mixture of the film-forming and non-film-forming dispersions according to the invention gives a considerable improvement, namely a decrease in the variation coefficient parallel to a certain increase (9585 cpm : 16636 cpm) in the region of the best results at the highest concentrations used.

At the lower concentrations of the data, the difference between coating with the film-forming dispersion alone versus coating with a mixture of film-forming and non-film-forming dispersion runs up against a lack of a significant increase in test sensitivity.

The best results are given by beads which are coated according to the invention with a latex of a dispersion mixture which contains 10-20 weight percent of the film-forming dispersion. Compared with uncoated polystyrene beads (which serve as "state of the art"), polystyrene beads coated with the mixture of film-forming dispersion and non-film-forming dispersion show an at least four-fold increase in the measured counts per minute (cpm) values in the lower and middle concentrations ranges of the data, which extends even up to the second highest concentration. Even at the highest concentration there is an increase in the measured cpm values by a factor of about 2.5. The advance achieved in the technology of solid body immunoassays can thus be considered to be clearly demonstrated.

TABLE 1

Results with Uncoated Polystyrene Beads

| cpm Measurement after 5 Minutes | Average | Variation Coefficient (%) | Concentration of Antigen (ng/ml) |
|---|---|---|---|
| 0.6 | 3.3 | 157.8 | 0 |
| 0.0 | | | |
| 9.3 | | | |
| 11.8 | 11.9 | 43.0 | 0.016 |
| 17.0 | | | |
| 6.8 | | | |
| 23.2 | 22.4 | 39.3 | 0.062 |
| 30.7 | | | |
| 13.2 | | | |
| 52.4 | 56.9 | 13.8 | 0.218 |
| 52.3 | | | |
| 56.9 | | | |
| 213.7 | 204.2 | 5.1 | 0.700 |
| 205.6 | | | |
| 193.1 | | | |
| 1299.8 | 929.6 | 43.5 | 2.980 |
| 750.0 | | | |
| 738.8 | | | |
| 2891.3 | 3089.9 | 16.1 | 11.80 |
| 2724.6 | | | |
| 10872.2 | 9585.7 | 29.6 | 50.80 |
| 11561.9 | | | |
| 6322.9 | | | |

TABLE 2

Results with Polystyrene Beads Coated Only with Non-Film-Forming Dispersion (Example 3)

| cpm Measurement after 5 Minutes | Average | Variation Coefficient (%) | Concentration of Antigen (ng/ml) |
|---|---|---|---|
| 23.6 | 28.8 | 21.3 | 0 |
| 22.4 | | | |
| 29.3 | | | |
| 52.3 | 44.8 | 20.0 | 0.016 |
| 47.1 | | | |
| 34.8 | | | |

TABLE 2-continued

Results with Polystyrene Beads Coated Only with Non-Film-Forming Dispersion (Example 3)

| cpm Measurement after 5 Minutes | Average | Variation Coefficient (%) | Concentration of Antigen (ng/ml) |
|---|---|---|---|
| 93.5 | 90.1 | 3.4 | 0.062 |
| 87.9 | | | |
| 88.9 | | | |
| 269.4 | 274.6 | 1.7 | 0.218 |
| 278.2 | | | |
| 276.2 | | | |
| 889.6 | 882.4 | 3.0 | 0.700 |
| 853.6 | | | |
| 904.9 | | | |
| 3227.2 | 3242.5 | 0.7 | 2.980 |
| 3266.7 | | | |
| 3233.4 | | | |
| 10768.1 | 11016.4 | 2.2 | 11.80 |
| 11230.9 | | | |
| 11051.1 | | | |
| 23203.6 | 23266.7 | 0.3 | 50.80 |
| 23339.7 | | | |
| 23258.4 | | | |

TABLE 3

Results with Polystyrene Beads Coated with the Dispersions (Example 3 - Non-Film-forming) and (Example 2 - Film-forming) in a Ratio by Weight of 90:10

| cpm Measurement after 5 Minutes | Average | Variation Coefficient (%) | Concentration of Antigen (ng/ml) |
|---|---|---|---|
| 19.7 | 24.0 | 18.7 | 0 |
| 23.6 | | | |
| 28.6 | | | |
| 66.8 | 64.4 | 9.6 | 0.016 |
| 68.9 | | | |
| 57.4 | | | |
| 133.6 | 125.0 | 6.7 | 0.062 |
| 124.2 | | | |
| 117.0 | | | |
| 371.3 | 360.5 | 3.8 | 0.218 |
| 345.5 | | | |
| 364.6 | | | |
| 1108.7 | 1127.4 | 2.0 | 0.700 |
| 1151.4 | | | |
| 1121.0 | | | |
| 4165.3 | 4148.6 | 1.6 | 2.980 |
| 4076.9 | | | |
| 4203.4 | | | |
| 13811.1 | 13988.1 | 1.2 | 11.80 |
| 14083.3 | | | |
| 14100.2 | | | |
| 27782.0 | 28598.4 | 2.8 | 50.80 |
| 28631.9 | | | |
| 29383.4 | | | |

TABLE 4

Results with Polystyrene Beads Coated with a Mixure of the Dispersion (Example 3 - Non-Film-forming) and (Example 2 - Film-forming) in a Ratio by Weight of 90:10

| cpm Measurement after 5 Minutes | Average | Variation Coefficient (%) | Concentration of Antigen (ng/ml) |
|---|---|---|---|
| 24.7 | 28.4 | 22.7 | 0 |
| 24.6 | | | |
| 35.8 | | | |
| 51.4 | 55.7 | 6.8 | 0.016 |
| 58.7 | | | |
| 56.8 | | | |
| 117.0 | 114.7 | 2.5 | 0.062 |
| 115.4 | | | |
| 111.6 | | | |
| 350.3 | 345.2 | 2.3 | 0.218 |
| 348.8 | | | |
| 336.3 | | | |
| 1054.3 | 1074.7 | 4.1 | 0.700 |

TABLE 4-continued

Results with Polystyrene Beads Coated with a Mixure of the Dispersion (Example 3 - Non-Film-forming) and (Example 2 - Film-forming) in a Ratio by Weight of 90:10

| cpm Measurement after 5 Minutes | Average | Variation Coefficient (%) | Concentration of Antigen (ng/ml) |
|---|---|---|---|
| 1044.9 | | | |
| 1124.7 | | | |
| 3981.6 | 3941.7 | 1.0 | 2.980 |
| 3904.3 | | | |
| 3940.4 | | | |
| 13249.4 | 13070.7 | 1.4 | 11.80 |
| 12887.8 | | | |
| 13074.8 | | | |
| 27895.8 | 28372.2 | 2.4 | 50.80 |
| 29123.3 | | | |
| 38097.4 | | | |

TABLE 5

Results with Polystyrene Beads Coated with a Mixure of the Dispersion (Example 3 - Non-Film-forming) and (Example 2 - Film-forming) in a Ratio by Weight of 50:50

| cpm Measurement after 5 Minutes | Average | Variation Coefficient (%) | Concentration of Antigen (ng/ml) |
|---|---|---|---|
| 78.6 | 46.7 | 46.7 | 0 |
| 28.9 | | | |
| 32.6 | | | |
| 57.3 | 55.7 | 5.2 | 0.016 |
| 52.9 | | | |
| 57.3 | | | |
| 99.8 | 104.8 | 4.8 | 0.062 |
| 104.6 | | | |
| 109.8 | | | |
| 338.1 | 327.4 | 2.9 | 0.218 |
| 322.2 | | | |
| 321.9 | | | |
| 982.4 | 1012.4 | 3.3 | 0.700 |
| 1006.4 | | | |
| 1048.2 | | | |
| 3531.1 | 3673.7 | 3.4 | 2.980 |
| 3741.1 | | | |
| 3749.6 | | | |
| 12408.6 | 12371.6 | 0.9 | 11.80 |
| 12242.5 | | | |
| 12463.8 | | | |
| 26464.6 | 26944.0 | 2.9 | 50.80 |
| 26530.6 | | | |
| 27838.8 | | | |

TABLE 6

Results with Polystyrene Beads Coated with a Mixure of the Dispersion (Example 1 - Film-forming) and (Example 3 - Non-Film-forming) in a Ratio by Weight of 80:20

| cpm Measurement after 5 Minutes | Average | Variation Coefficient (%) | Concentration of Antigen (ng/ml) |
|---|---|---|---|
| 18.7 | 26.4 | 27.3 | 0 |
| 27.6 | | | |
| 33.0 | | | |
| 47.6 | 52.9 | 8.9 | 0.016 |
| 54.8 | | | |
| 56.3 | | | |
| 103.9 | 98.2 | 5.1 | 0.062 |
| 95.9 | | | |
| 94.8 | | | |
| 304.7 | 300.8 | 2.0 | 0.218 |
| 294.0 | | | |
| 303.7 | | | |
| 865.8 | 885.2 | 3.4 | 0.700 |
| 870.4 | | | |
| 919.3 | | | |
| 3396.1 | 3317.7 | 2.5 | 2.980 |
| 3231.9 | | | |
| 3326.0 | | | |
| 11132.8 | 10965.4 | 1.4 | 11.80 |

TABLE 6-continued

Results with Polystyrene Beads Coated with a Mixure of the Dispersion (Example 1 - Film-forming) and (Example 3 - Non-Film-forming) in a Ratio by Weight of 80:20

| cpm Measurement after 5 Minutes | Average | Variation Coefficient (%) | Concentration of Antigen (ng/ml) |
|---|---|---|---|
| 10865.5 | | | |
| 10899.1 | | | |
| 22130.6 | 22269.8 | 0.6 | 50.80 |
| 22364.9 | | | |
| 22313.9 | | | |

TABLE 7

Results with Polystyrene Beads Coated Only with Film-Forming Dispersion (Example 2)

| cpm Measurement after 5 Minutes | Average | Variation Coefficient (%) | Concentration of Antigen (ng/ml) |
|---|---|---|---|
| 41.4 | 36.3 | 20.9 | 0 |
| 27.6 | | | |
| 39.9 | | | |
| 42.9 | 46.8 | 7.6 | 0.016 |
| 49.8 | | | |
| 47.6 | | | |
| 90.9 | 78.3 | 14.6 | 0.062 |
| 75.1 | | | |
| 68.8 | | | |
| 241.8 | 283.3 | 3.3 | 0.218 |
| 243.6 | | | |
| 229.5 | | | |
| 698.9 | 706.9 | 6.8 | 0.700 |
| 663.8 | | | |
| 757.8 | | | |
| 2747.1 | 2663.4 | 4.1 | 2.980 |
| 2700.0 | | | |
| 2543.3 | | | |
| 8310.1 | 8124.4 | 2.4 | 11.80 |
| 8138.1 | | | |
| 7925.8 | | | |
| 17829.9 | 16556.0 | 8.0 | 50.80 |
| 15204.7 | | | |
| 16635.9 | | | |

Example 15

Binding of Trypsin to the Product of Example 16

500 mg of trypsin (bovine, Art. No. 24 579, 40 v/mg; E. Merck, Darmstadt) are dissolved in 10 ml of 1 molar potassium phosphate buffer (pH 7.5) and added to 5 g of the inert carrier material of following Example 16.

The mixture is shaken for 10 seconds and let stand for 72 hours at 23° C. It is then washed seven times with portions of deionized water, each ten-fold by volume, and three times with portions of 1.0 molar phosphate buffer (containing 500 ppm of p-hydroxybenzoic acid for preservation and 2 percent of 2-propanol), each 10-fold by volume.

Washed (on a frit over vacuum) the moist yield is: 5.6 g. Activity toward BAEE : 3.2 U/g Casein : 0.36 U/g.

In comparison with the state of the art, there is no loss in activity by coating.

One unit (U) of enzyme activity toward BAEE is the amount of enzyme which will hydrolyze one micromole of BAEE per minute at pH 8.0 and 34° C. (cf. A. Lauwers et al., *Pharmaceutical Enzymes*, Scientia, Ghent).

Determination of Activity toward Casein, a High Molecular Weight Substrate

Substrate 350 ml of deionized water and 32 ml of 0.5 molar NaOH are added to 20 g of casein according to Hammarstein (Art. No. 2242, E. Merck, Darmstadt) and stirred at 60° C. until the casein is dissolved. After cooling to room temperature, the pH value is adjusted to pH 8.0 by the addition of 0.1 molar HCl. Then the mixture is brought to a volume of 500 ml with deionized water. (It should be noted that because of the aggregation of casein, the solution is always somewhat cloudy.)

Determination 20 ml of substrate solution and 2 g of the product of Example 15 are stirred at 37° C. and pH 8.0 in a reaction vessel equipped with a thermostat and an apparatus maintaining constant pH. At the same time, the amount of hydrolyzed substrate is recorded by noting the consumption of 0.01 molar NaOH versus time.

After 10 minutes of incubation, the product is caught in a glass frit (porosity No. 2) and the same product is incubated for a further 10 minutes. This cycle was repeated.

For a determination of activity, the 4th cycle is evaluated.

Activity toward N-Benzoyl-L-Arginine Ethyl Ester Hydrochloride (BAEE), a Low Molecular Weight Substrate Substrate 1% BAEE solution (Art. No. 1672, E. Merck, Darmstadt) is dissolved in 0.05 molar potassium phosphate buffer (pH 7.5).

Incubation 20 ml of substrate solution and 2 g of the product of Example 17 (weight moist) are titrated at 37° C. and pH 7.5 with 0.1 molar NaOH.

Incubation time: 10 minutes. The cycle of incubation, recovery, and determination is repeated.

For determining activity, the 4th cycle is consulted.

Example 16

Coating of Inert Carrier Material in the Form of Polymer Beads 900 g of polymethyl methacrylate beads having an average particle diameter of 310 microns are coated in a fluidized bed apparatus (Uniglatt, Glatt Company) with the following dispersion mixture:

| | |
|---|---|
| Non-film-forming dispersion (Example 7) | 3150 g |
| Film-forming dispersion (Example 4) | 1350 g |
| | 4500 g |

Ratio of Core/Shell=1:1 (dry weight of polymers in dispersion)
Process conditions
Spraying pressure: 1.8 bar
Air inlet temperature: 40°-50° C.
Air outlet temperature: 19°-23° C.
Spray velocity: 11.84 g/min
The product obtained is dried under vacuum for 24 hours. It is free-flowing and 85.8 weight percent of the yield is in the particle size range of 0.3-0.6 mm.

Activity after the bonding of trypsin:
BAEE: 3.9 U/g Casein: 1.04 U/g

Example 17

The Coating of Inert Carrier Material in the Form of Polystyrene Beads 700 g of polymethyl methacrylate beads having an average particle diameter of 310 microns are coated in a fluidized bed apparatus (Uniglatt, Glatt Company) with the following dispersion mixture:

| | |
|---|---|
| Non-film-forming Dispersion (Example 7) | 1225 g |
| Film-forming Dispersion (Example 10) (diluted to 20% dry solids) | 525 g |
| | 1750 g |

Ratio of Core : Shell=2:1 (dry weight of polymers in dispersion)
Process Conditions
Spray pressure: 1.8 bar
Air inlet temperature: 40° C.
Air outlet temperature: 23°-25° C.
Spray velocity: 8.75 g/min
The product obtained is dried under vacuum for 24 hours. It is free-flowing and, according to vibrating sieve analysis, 81.4 weight percent of the yield is in the range 0.3-0.6 mm.
Activity after the bonding of trypsin:
BAEE: 0.7 U/g Casein: 0.3 U/g Example 18

Coating of Inert Carrier Material in the Form of Polymer Beads 900 g of polymethyl methacrylate bead polymer having an average particle diameter of 310 microns is coated in a fluidized bed apparatus (Uniglatt, Glatt Company) with 1575 g of the dispersion of Example 5.
Ratio of Core : Shell: 3:1 (dry weight of polymers in dispersion)
Process Conditions
Spraying pressure: 1.8 bar
Air inlet temperature: 40°-45° C.
Air outlet temperature: 20°-23° C.
Spray velocity: 8.75 g/min
The product obtained is dried under vacuum for 24 hours. It is free-flowing and 62.2 weight percent of the yield is in the particle size region of 0.3-0.6 nun.
Activity after the bonding of trypsin:
BAEE : 0.3 U/g Casein : 0.9 U/g.

Example 19

Coating of Inert Carrier Material in the Form of Polymer Beads 775 g of polymethacrylate beads ("Plexidon M449") having an average particle diameter of 100 microns are coated in a fluidized bed apparatus (Uniglatt, Glatt Company) with the following dispersion mixture:

| | |
|---|---|
| Dispersion of Example 6: | 1803.33 g |
| Dispersion of Example 8: | 775.00 g |
| | 2583.33 g |

Ratio of Core/Shell: 1:1 (dry weight of polymers in dispersion)
Process Conditions Spraying Pressure: 2 bar
Air inlet temperature: 40°–45° C.
Air outlet temperature: 22°–25° C.
Spray velocity: 10.5 g/min
Drying: 24 hours under vacuum
The product obtained is free-flowing and white. The average particle size is 189 microns.

Example 20

In analogy to Examples 2 and 3 above, the following filmforming and non-forming dispersions have been prepared, the difference being that glycidylmethacrylate as a monomer carrying a functional group has been replaced by the following monomers in identical amounts by weight:

i) methacrylic anhydride
ii) acrolein
iii) 2-(acetoacetoxy)ethyl methacrylate
iv) acrylamido glycolic acid, methyl ester
v) 2-(chloroacetoxy)-2-ethyl methacrylate
vi) 2-chloroethyl methacrylate The dispersions obtained in this fashion are functionally comparable to those obtained in Examples 2 or 3, respectively. They are also used in preparing carrier systems for bonding biologically active material in close analogy to Examples 11 and 12 and they yield similar results.

What is claimed is:

1. A method for making a carrier for the covalent bonding thereto of a biologically active material, which method comprises coating a solid support with a dispersion of a film-forming polymer and with another dispersion of a non-film-forming polymer, at least one of the polymers including a monomer having at least one functional group capable of covalently bonding with the biologically active material.

2. A method as in claim 1 wherein the support is coated with a mixture of the dispersions.

3. A method as in claim 1 wherein the support is inorganic.

4. A method as in claim 1 wherein the support is organic.

5. A method as in claim 1 wherein the support is in the form of spherical particles.

6. A method as in claim 5 wherein the spherical particles have an average diameter from 0.01 to 10 millimeters.

7. A method as in claim 1 wherein the polymers each comprise at least one monomer selection from the group consisting of acrylates, methacrylates, styrene, alkyl styrenes, vinyl esters, and vinyl halides.

8. A method as in claim 1 where the polymer in at least one of the dispersions comprises at least one monomer of the formula $Z\text{-}(R)_n\text{-}X$, wherein X is a functional group selected from the group consisting of sulfonic acid halide, thioisocyanate, thiocarbonyldioxy, carbonyl-imidoyldioxy, haloethoxy, aziridine, epoxy, formyl, keto, acryloyl, anhydride, and active ester groups, R is a chemically inert spacer, n is 0 or 1, and Z is a polymerizable entity.

9. A method as in claim 1 wherein the polymers each comprise at least one monomer, different from the monomer having at least one functional group, selected from the group consisting of acrylates, methacrylates, styrene, alkyl styrenes, vinyl esters, and vinyl halides.

10. A method as in claim 9 where the polymer in at least one of the dispersions comprises at least one monomer of the formula $Z\text{-}(R)_n\text{-}X$, wherein X is a functional group selected from the group consisting of sulfonic acid halide, thioisocyanate, thiocarbonyldioxy, carbonyl-imidoyldioxy, haloethoxy, aziridine, epoxy, formyl, keto, acryloyl, anhydride, and active ester groups, R is a chemically inert spacer, n is 0 or 1, and Z is a polymerizable entity.

11. A method as in claim 1 wherein the monomer having at least one functional group is present in the non-film-forming polymer.

12. A method as in claim 1 wherein the monomer having at least one functional group is present in an amount from 0.1 to 80 percent by weight of the film-forming polymer or of the non-film-forming polymer.

13. A method as in claim 1 wherein the polymers each further comprise at least 50 percent by weight of monomers of the formula 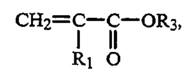 wherein $R_1$ is hydrogen, methyl, or $—CH_2—COOR_2$, $R_2$ is alkyl having 1 to 4 carbon atoms, and $R_3$ is linear or branched alkyl having 1 to 18 carbon atoms or is cycloalkyl having 3 to 12 ring members.

14. A method as in claim 11 wherein the film-forming polymer has a minimum film forming temperature below 60° C.

15. A method as in claim 14 wherein the non-film-forming polymer has a freezing point of at least 30° C.

16. A method as in claim 1 wherein the film-forming polymer is present in the film-forming dispersion as particles having an average particle size from 0.02 to 5 microns.

17. A method as in claim 1 wherein the non-film-forming polymer is present in the non-film-forming polymer dispersion as particles having an average particle size from 0.04 to 5 microns.

18. A method as in claim 11 wherein the polymers in the film-forming and non-film-forming dispersions are present as particles and the average size of the particles in the non-film-forming dispersion is larger than the average size of the particles in the film-forming dispersion by a factor of 1.2 to 20.

19. A method as in claim 11 wherein the ratio by dry weight of polymer in the non-film-forming dispersion to dry weight of polymer in the film-forming dispersion is from 50:50 to 99:1.

20. A method as in claim 1 wherein the support is coated by immersion or spraying.

21. A method as in claim 2 wherein the support is coated by immersion or spraying.

* * * * *